(12) United States Patent
Pamment

(10) Patent No.: US 9,821,150 B2
(45) Date of Patent: Nov. 21, 2017

(54) MEDICAL DEVICE

(71) Applicant: DENKE MEDICAL LTD, Reading (GB)

(72) Inventor: Keith Robert Pamment, Maidenhead Berkshire (GB)

(73) Assignee: Denke Medical Ltd., Reading (GB)

( * ) Notice: Subject to any disclaimer, the term of this patent is extended or adjusted under 35 U.S.C. 154(b) by 0 days.

(21) Appl. No.: 14/779,402

(22) PCT Filed: Mar. 24, 2014

(86) PCT No.: PCT/GB2014/050909
§ 371 (c)(1),
(2) Date: Sep. 23, 2015

(87) PCT Pub. No.: WO2014/155075
PCT Pub. Date: Oct. 2, 2014

(65) Prior Publication Data
US 2016/0051808 A1 Feb. 25, 2016

(30) Foreign Application Priority Data

Mar. 25, 2013 (GB) .................................. 1305378.0

(51) Int. Cl.
*A61M 39/02* (2006.01)
(52) U.S. Cl.
CPC ..... *A61M 39/0208* (2013.01); *A61M 39/0247* (2013.01); *A61M 2039/0238* (2013.01);
(Continued)

(58) Field of Classification Search
CPC ...... A61M 39/0208; A61M 2039/0238; A61M 25/02; A61M 2025/0266;
(Continued)

(56) References Cited

U.S. PATENT DOCUMENTS

| 2,902,146 A | * | 9/1959 | Doherty | ................ A61F 15/001 |
| | | | | 206/361 |
| 3,234,941 A | * | 2/1966 | Tucker | ................ A61F 13/0226 |
| | | | | 128/888 |

(Continued)

FOREIGN PATENT DOCUMENTS

| CN | 202191579 U | 4/2012 |
| CN | 202191579 U | 10/2014 |

(Continued)

OTHER PUBLICATIONS

Uzawa, M. et al., English abstract only of Japanese Application No. 2010172653, Cement Composition for Road, publication date Feb. 16, 2012, one page.

(Continued)

*Primary Examiner* — Shefali Patel
(74) *Attorney, Agent, or Firm* — Polsinelli PC

(57) ABSTRACT

A device for positioning a subcutaneous port during an access procedure, said device comprising a dome (1) of plastic material, said dome being shaped to fit directly over the subcutaneous port, and a flange (3) extending laterally from the dome which is able to contact a surrounding skin area, wherein the device is a unitary device which is configured to be deformable or fracturable so as to facilitate removal of the device from the surrounding skin area.

14 Claims, 5 Drawing Sheets

(52) U.S. Cl.
CPC ............... *A61M 2039/0258* (2013.01); *A61M 2039/0276* (2013.01); *A61M 2039/0288* (2013.01)

(58) Field of Classification Search
CPC ...... A61M 2025/0273; A61M 39/0247; A61M 2039/0258; A61M 2039/0288; A61M 2039/0294
See application file for complete search history.

(56) References Cited

U.S. PATENT DOCUMENTS

| | | | |
|---|---|---|---|
| 4,579,120 A | | 4/1986 | MacGregor |
| 4,633,863 A | * | 1/1987 | Filips .................... A61M 25/02 128/846 |
| 4,675,006 A | * | 6/1987 | Hrushesky ............ A61M 25/02 128/DIG. 26 |
| 4,857,053 A | | 8/1989 | Dalton |
| 4,915,694 A | | 4/1990 | Yamamoto et al. |
| 5,137,529 A | | 8/1992 | Watson et al. |
| 5,620,419 A | * | 4/1997 | Lui ........................ A61M 5/427 604/116 |
| 5,797,954 A | | 8/1998 | Shaffer et al. |
| 6,241,715 B1 | * | 6/2001 | Houser .................... A61F 7/02 450/37 |

FOREIGN PATENT DOCUMENTS

| | | |
|---|---|---|
| FR | 2521431 | 8/1983 |
| JP | 2010172653 | 8/2010 |

OTHER PUBLICATIONS

Lerol, A., English abstract only of French Application No. FR19860000056 also published as FR2592585, Device Facilitating the Injection of a Liquid Substance into the Reservoir Implanted Beneath the Skin for Supplying a Catheter, Jul. 10, 1987, one page.
International Search Report and Written Opinion dated Jul. 2, 2014, regarding PCT/GB2014/050909, 13 pages.
Search Report dated Aug. 28, 2013 regarding GB1305378.0, 3 pages.

* cited by examiner

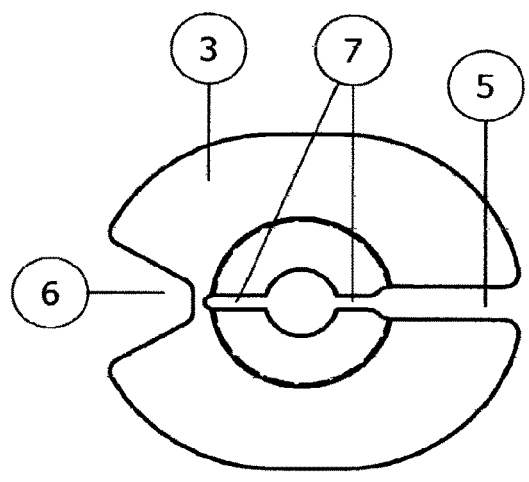
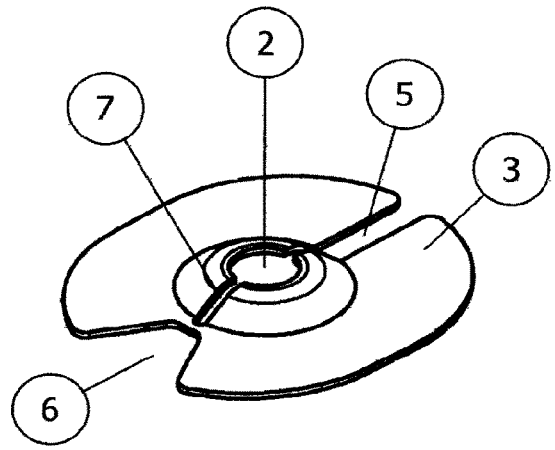
Figure 4
Figure 5
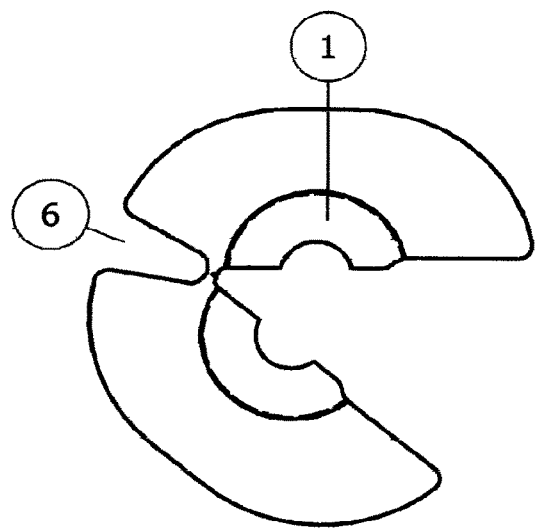
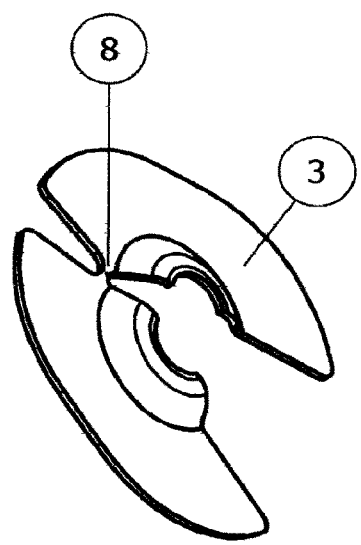
Figure 6
Figure 7

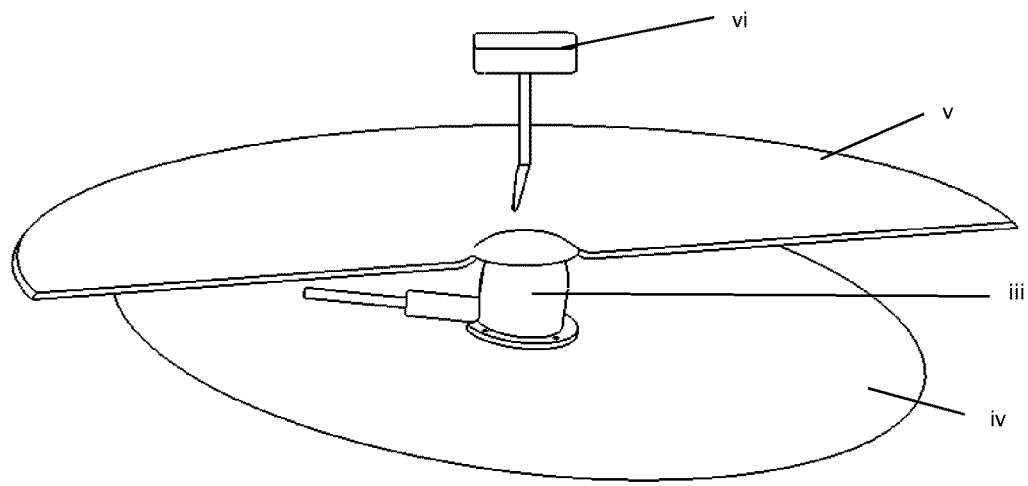
Figure 12A - PRIOR ART
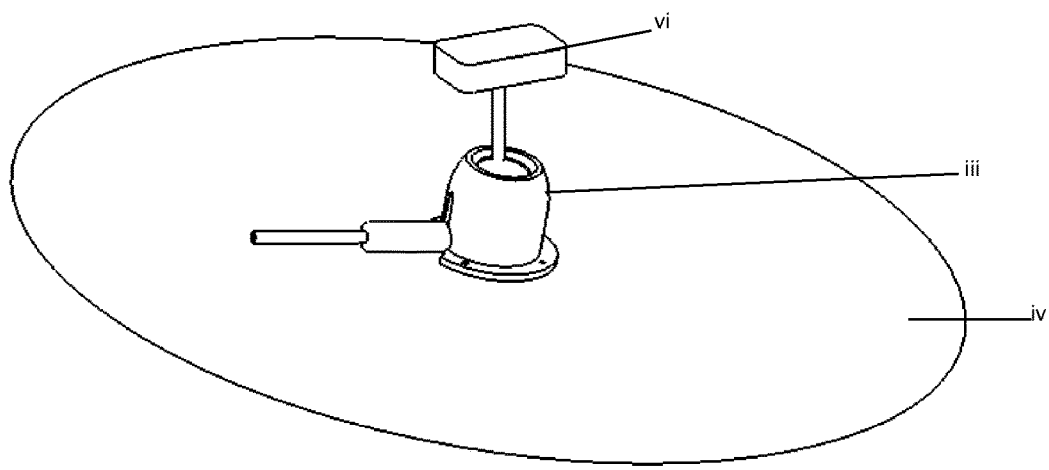
Figure 12B - PRIOR ART

MEDICAL DEVICE

CROSS REFERENCE TO RELATED APPLICATIONS

This application is a U.S. National Application filed under 35 U.S.C. 371 of PCT Application No. PCT/GB2014/050909, filed on Mar. 24, 2014, which claims priority to GB 1305378.0, filed in the United Kingdom, on Mar. 25, 2013, both of which are hereby incorporated by reference in their entirety.

FIELD OF THE INVENTION

The present invention relates to a device useful in the administration of drugs in particular where these are administered using a port or portacath, or other central venous access devices.

BACKGROUND OF THE INVENTION

Many intensive medical treatments currently available require patients to have repeated injections of drugs. In circumstances where intravenous access is proven to be limited, patients may be advised to have a central venous access device such as a port or portacath surgically implanted beneath the skin. Various types of ports or portacaths are available and are available under trade names such as Port-a-Cath, Microport, Bardport, PowerPort (power injectable), Passport, Infuse-a-Port, Medi-Port, and Lifesite (for hemodialysis patients). Ports of this type may form part of what is known as a totally implantable venous access system (TIVAS). Long-term intravenous lines, in particular those used with the TIVAS mentioned above can cause in significant damage to the veins.

In general, the port comprises a reservoir compartment or portal, made up of a solid casing provided with an upper septum comprising a self-sealing material such as a self-sealing silicone. It further comprises a plastic tube that extends from the reservoir and forms a catheter.

In use, the port is surgically inserted under the skin in one of a number of possible locations around the body including the upper chest or in the arm of a patient where it projects upwardly and appears as a small bubble in the skin. The catheter that extends from the reservoir is surgically inserted into a vein, such as the jugular vein, subclavian vein, or superior vena cava.

To administer treatment using this system, the port is located and the surrounding area is disinfected. Treatments may be administered by accessing the port through the overlying skin and the septum using a needle such as a Huber needle. Treatments delivered via this route will be transfused readily throughout the body as they will pass directly into the vein via the catheter.

Ports of this type may be used in a variety of treatments including for example total parenteral nutrition, delivery of infusions in chemotherapy, delivery of coagulation factors, the withdrawing of blood from patients requiring frequent blood tests, delivery of antibiotics such as are used in the treatment of long-term conditions such as cystic fibrosis, and the delivery of various medications.

However, ports are of limited life and will need to be replaced at intervals. Although they may last 5-6 years, failure in much shorter periods, for example of 2 years or less are not uncommon. When the device fails, a further surgical operation is required to remove the port and to replace it with a new one at a different site within the body. As there are limited sites available for insertion of a port or portacath, it is important for patients who are likely to have a long term need of the port, such as cystic fibrosis patients, to ensure that the life of a port is as long as possible.

One reason for premature failure of a portacath is believed to the result of incorrect needle insertion. Inspection of portacaths that have failed after removal can reveal problems. In particular, needle insertion marks visible in the septum may be grouped closer to one side of the septum, or needle hits may also be found on the side walls of the casing of the portacath. Indeed, cracks through the casing are also found. These are very likely to be a direct result of the needle being inserted off-centre.

The usual procedure for inserting needles into a port is a manual one. After disinfection of the area over and around the port, a medical practitioner such as a nurse or doctor will hold the port with two or three fingers of one hand whilst inserting the needle with the other hand. During this manoeuvre, it can be difficult to hold the port still whilst inserting the needle. This is due to the fact that the port is attached to the inside of the body, which in itself is dynamic and is therefore prone to movement. FIG. 12A below shows a three-dimensional model of a port underneath the skin. The port (iii) is fixed to the subcutaneous body tissue (iv) but this means that it can pivot in any direction relative to the skin (v). The skin is fixed and the needle (vi) can move up and down along the central axis of the raised dome of the skin. Under these circumstances, although a needle looks like it is central to the port, FIG. 12B, in which the skin layer is removed, shows that the needle is in fact off-centre.

If the needle is not inserted centrally in the septum, it may strike the casing leading to pitting or cracking of the portacath and leading to premature failure.

Devices for facilitating accurate positioning of the needle are described for example in Japanese patent application No. JP2010172653 and U.S. Pat. No. 5,620,419. These provide for locator devices arranged to fit over the port whilst a needle is inserted into it. However, such devices are not readily available. One reason why such devices have not been widely adopted may be associated with the ease of use.

Once the needle is in position in the port, it is necessary to remove the locator from the vicinity of the needle, to allow the infusion process to proceed. JP2010172653 does not generally address this problem, although one embodiment is constructed in a two-part form that includes a complex comb structure to join the two elements together. This embodiment is a complex arrangement, which would be difficult to manufacture economically. In addition, the elements of the comb-like structure extend across the opening through which the needle is inserted, and so these elements may interfere with the injection and removal operation, potentially damaging the port.

The device of U.S. Pat. No. 5,620,419 provides an upwardly projecting flange to allow the device to be slid off. However, this is a delicate operation as the needle and wide pad at the top of the needle (found on the modern huber needles) if present is required to pass through a narrow radial slit increasing the risk of disturbance to the needle. Furthermore, the upwardly projecting flange may interfere with the injection operation itself.

SUMMARY OF THE INVENTION

The applicants have produced a device that facilitates access to the port and may also reduce the likelihood of premature portacath failure by incorrect needle insertion, but which has the added benefit of being easy to use, and in particular to be readily removable once a needle is in position in a port.

According to the present invention, there is provided a device for positioning a subcutaneous port during an access procedure, said device comprising a dome of plastic material, said dome being shaped to fit directly over a subcutaneous port, a flange extending laterally from a base of the dome which flange is able to contact the surrounding skin area.

BRIEF DESCRIPTION OF THE DRAWINGS

The invention will now be particularly described by way of example with reference to the accompanying drawings in which:

FIG. 4 is a top view of an alternative form of device of the invention;

FIG. 5 is a perspective view of the device of FIG. 4;

FIG. 6 is a top view of the device of FIG. 4, after use where it has been deformed to allow removal;

FIG. 7 is a perspective view of the device of FIG. 6;

FIG. 12A shows a 3-dimensional conceptual model of a portacath in place underneath the skin with a Huber needle ready for insertion in what appears to be a central region of the port; and FIG. 12B is similar to FIG. 12A but with the model skin removed illustrating the actual position and angle of the needle when it is inserted into the port.

DETAILED DESCRIPTION

Figure 1:
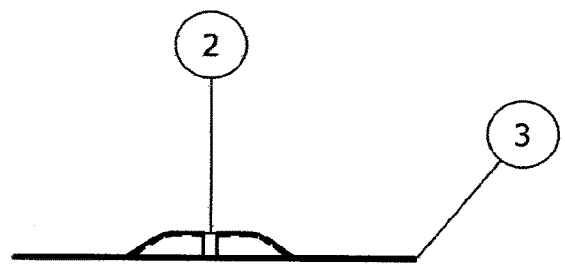
FIG. 1 is a side view of a device in accordance with the invention.
Figure 2:
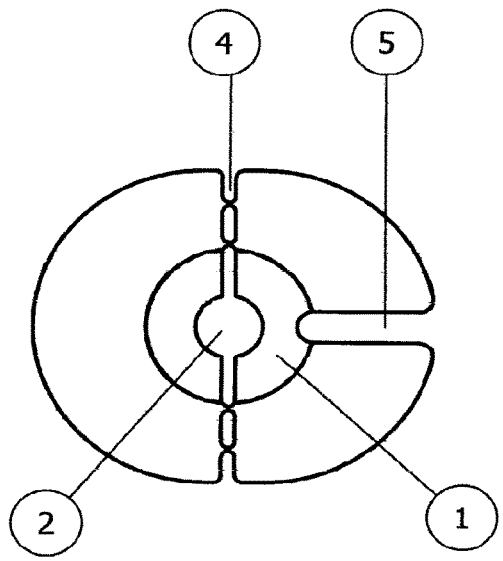
FIG. 2 is a top view of the device of FIG. 1.
Figure 3:
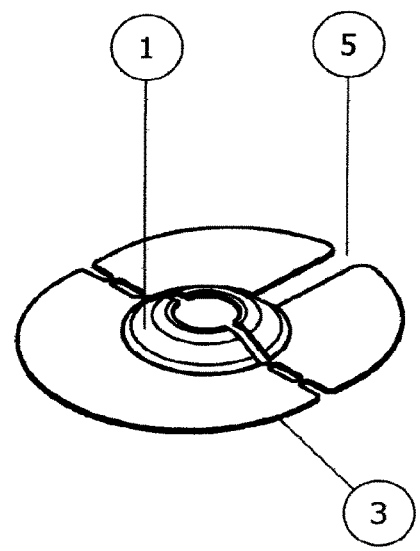
FIG. 3 is a perspective view of the device of FIG. 1.

In particular the device is a unitary device provided with a means facilitating removal by deformation or fracture of the device. By incorporating removal means of this type into the device, the device can be produced economically and easily as a single integrated structural element and furthermore is easy to use, and in particular to remove once the needle is in place.

If the device of the invention is pressed against the subcutaneous port so that the dome encompasses the port and the flange abuts the surrounding skin, the skin and subcutaneous body tissue are effectively pulled into alignment. As a result, injection through a central region of the dome will enter the port through a central region of the septum, reducing the risks of needle strikes on the casing and thus reducing the risk of premature failure.

The device is suitably of a plastics material, and in particular a medical grade plastic such as silicone rubbers, polyethylene such as ultrahigh molecular weight polyethylene (UHMWPE), polypropylene or polyacrylate such as poly(methyl methacrylate) (PMMA). The material should be pliable enough to allow it to form a cohesive fit to the body in the area of the port, but also rigid enough to ensure that, when in position on the skin, the device retains the adjacent skin and subcutaneous tissue in a fixed relationship. In general, this may be achieved if the plastic material is a substantially rigid plastic material, for instance with an elasticity modulus in the range of from 0.1-5 GPa, for example at about 1-1.5 GPa. However, to facilitate removal of the device using the removal means, the plastics should be relatively easily deformable or breakable. The tensile stress at yield may suitably be in the range of from 25-40 MPa, for example from 30-35 MPa. A particularly suitable material is a polypropylene homopolymer, sold as Purell HP371P (Lyondell Basel Holdings BV).

The dome and flange are suitably made in a single piece by processes such as moulding including injection moulding, but also by processes such as three-dimensional printing. The thickness of the device is suitably in the range of from 0.1-5 mm, in particular between 0.1 and 2 mm. The thickness of the plastic in the region of the dome may be different to that in of the flange. For instance, the dome may have a thickness in the range of from 0.5-1.5 mm, whilst the flange is from 0.1-1 mm in thickness.

It may be opaque and coloured or transparent, and in particular is transparent.

The dome of the device is shaped to fit snuggly over a port when it is in position subcutaneously. The precise shape of the dome may therefore vary depending upon the particular port that is being used. Typically however, the dome will be generally circular in cross-section with a diameter in the range of from 5-100 mm, for example from 5-80 mm such as from 5-50 mm, and in particular from 10-30 mm. The distance the dome extends in an upwards direction is similarly variable depending upon the specific port being used but will typically be in the range of from 3-20 mm, for example about 4 mm.

The dome is suitably profiled so as to match the profile of the port as closely as possible. Thus, for example, the dome may have a flattened top surface, forming a plateau region to ensure that it fits snugly onto a port.

In a particular embodiment, the device according to claim 1 or claim 2 wherein a central region of the dome is provided with indicator means which shows where the central region of the dome is positioned. The indicator means suitably defines an area within the central region, which, when the device is in position on a subcutaneous port, is directly aligned with a central region of the septum into which insertion of a needle is desirable. Thus the indicator means provides a suitable target for insertion of the needle.

The indicator means suitably comprises a simple line or mark in the plastic, or it may comprise an upwardly projecting ridge or barrier to define the area. In a particular embodiment however, the indicator means comprises a hole in the plastic of the dome. The hole means that the needle can be applied directly to the skin through the hole. In some cases, markers may also be provided around the hole, in particular line markers which are aligned with the centre of the hole, to facilitate accurate and central needle insertion.

The flange is of sufficient size and position to ensure that once in position, relative movement between the port and the skin and in particular any tipping movement is inhibited. It may extend in one or more directions. Typically, it will extend from 5 to 50 mm from the base of the dome. In a particular embodiment, the flange substantially surrounds the dome.

The flange may be of any shape such as circular, oval, square or rectangular shape, but will typically be circular in shape to ensure that the subcutaneous tissue is held consistently around the entire area of the port. It is generally flat or horizontally disposed, although it may be slightly inclined, in particular in a downwards direction.

When the flange surrounds the dome completely or substantially completely, it may be provided with a channel to accommodate the catheter line that extends from the port beneath the skin. This channel may also aid ultimate removal of the device from the skin as the sides can act as tabs which may be grasped for removal purposes, in particular where a cut-away section as described further below, is arranged directly opposite to the channel in the flange, so that the device can readily deform as described hereinafter. The channel is of a suitable size to allow it to fit comfortably over the catheter line when in position on the body. Suitably therefore, it will be from 0.5-1.5 cm wide.

The device is also provided with means to facilitate removal from the skin after a needle has been inserted into the port. The removal means may comprise perforations that allow the flange to be deformed, torn or cut for easy removal. Any perforations suitably extend across the width and/or the length of the flange at least, and they may also extend across the entire device including the dome so that the device may be removed effectively without any contact being made with the needle.

In a particular embodiment however, the removal means may take the form of a cut-away section within the flange which is arranged such that deformation of the device into the cut-away section opens up a central area of the dome, allowing easy removal of the device from the surface of the skin. In particular, the cut-away section, which may be extensive in area, is aligned with an opposing channel in the flange such that the cut-away section and the opposing channel are separated by a hinge region, and wherein rotation of the device around the hinge region causes a central area of the dome to open up. In this way, the device is simply and easily deformed and slid away after needle insertion.

The cut-away section may be of any suitable shape to allow the device to deform into the cut-away section whilst remaining essentially flat (in the x/y plane). For instance, the cut-away section may comprise a v-shaped opening in the side wall of the flange. The opening is relatively wide at the edge of the flange, for example extending from 40°-120° and suitably an inclusive 60° angle around the circumference of the flange, narrowing towards the dome. The cut-away section suitably terminates a short distance from the dome.

The cut-away section is arranged directly opposite a channel which extends across the dome and the opposing side of the flange. This channel is relatively narrow, in particular across the dome region to avoid reducing the rigidity of the dome structure significantly. In a particular embodiment, this opposing channel incorporates the channel described above which accommodate the catheter line, in which case, it will widen across the flange.

The cut-away section and the opposing channel do not join up, and so a portion of the body of the device remains intact, and this can act as a hinge region. In this embodiment, removal of the device is effected by deforming the device by rotating the opposing sides around he hinge region, such that the cut-away section closes up and the opposing channel is widened. In particular, the facing edges of the opposing channel can be rotated away in an opposing direction, or alternatively, one edge may be held still and the other slid away. This has the effect of substantially opening up a hole in the device through which the needle has been inserted.

Whilst the sides of the channel itself can be used as tabs to assist in the deformation of the device, pull-tabs may be provided on the edges of the flange to facilitate this. In addition, the surfaces of the pull-tabs may be modified, for example roughened, to provide improved grip to further facilitate the removal process. Suitably such tabs will extend substantially in the plane of the flange. They are suitably positioned at approximately 90° to an axis formed by the centre of the cut-away section and the opposing channel.

The hinge region is of a sufficient size and thickness to ensure that the device can deform easily whilst remaining in the x/y plane. If the hinge region is too thick or too rigid, the device may curl up or down when being deformed, for example during the pulling on the tabs.

The device may be reusable if sterilised but is conveniently produced in disposable form. It may be supplied in a sterile condition and packaged in a sterile container, which may form part of any kit supplied for use with infusions, needles etc, intended for use as described above. Thus in a further embodiment, the invention provides a kit comprising a device as described above, and one or more of disinfecting means, such as swabs or disinfectants, and a needle and in particular a Huber needle. Each of the elements of the kit is suitably sterile and packaged in a sealed package or compartment.

In a further aspect, the invention provides a method for accessing a subcutaneous port, said method comprising positioning a device as described above directly on said port so that the dome fits over the port and the flange makes direct contact with the surrounding area of skin, injecting into the port through a central region in the dome, and thereafter removing the device from the skin. By pressing the device of the invention directly against the subcutaneous port, the dome region interacts with the port and constrains it into alignment with the skin. As a result, the central region can be readily identified and the needle such as the Huber needle, inserted correctly into the centre of the septum of the port. During this operation, the flange may be slightly deformed which ensure that it maintains a tight fit against the skin. The catheter line extending from the port beneath the skin is suitably accommodated within a channel in the flange as described above.

The device may be removed after the needle is in position by sliding, cutting or tearing the device apart along a perforation line. If required, scissors can be used to assist in this. However, in a preferred embodiment, the device is removed by deforming it, in particular by rotating portions of the device around a hinge region as described above, so as to open up the hole in the device through which the needle has been inserted, to allow it to be slid easily away from the area without interacting with the needle itself.

The use of the device makes Huber needle insertion easier and therefore it may be carried out by a wider range of medical practitioners, even in a home environment. Furthermore, it is probable that correct and reliable insertion of needles into ports of this kind will increase the longevity of the port since it is less likely to failure due to misplaced needle strikes. If port life can be improved, then the patient will have to undergo fewer operations resulting in a reduced risk to patients and a saving of money and resources. In addition, with fewer port replacements, the problem of running out of places to have a port is reduced.

EXAMPLE 1

A device embodying the invention is shown in FIG. 1. It comprises a circular disc. A raised section or dome (1) is located towards the centre of the disc and is shaped with essentially the same profile as a portacath. There is a hole (2) provided centrally in the top of the dome (1). A substantially circular flange (3) extends outwardly from the base of the dome (1).

A radial section of the flange (3) is cut away to form a radial channel (5) extending outwardly from the raised section (1). In addition, a number of cutaways (4) with small tabs form perforations that extend radially out from the centre of the dome (1).

In use, the device, which is sterile, is applied to the skin of a patient in the region of a subcutaneous port. The dome (1) of the device is pressed into a position in which it surrounds and engages the casing of the port so that it prevents relative movement between the port and the location device in the x/y plane. The wide flat base of the device formed by the flange (3) is pressed against the skin, which action pulls the port down tight against the body and prevents relative movement between the port and the device in the z plane. Any bulges in the skin caused by the catheter line extending from the port can be accommodated within the channel (5). In this way, the dome (1) constrains the movement of the underlying portacath bringing it into alignment with the skin.

An injection using for instance a Huber needle can then be administered through the hole (2) which will be directly aligned with the central region of the septum of the portacath. The use of the device improves the visibility of the portacath location.

Once the needle is in place in the port, the device of the invention may be removed by tearing or cutting along the perforation lines (4), using scissors if required and then slid away.

EXAMPLE 2

An alternative form of the device of the invention is shown in FIGS. 4 to 8. In this embodiment, before use the flange (3) is provided with a cut-away section (6) arranged directly opposite the channel (5) for accommodating the catheter under the skin (FIGS. 4-5). In addition, a narrow cut-out (7) extends from the channel (5) across the dome (1) and through the hole (2) towards the cut-away section (6) leaving only a small bridging section (8) holding the device together.

Figure 11:
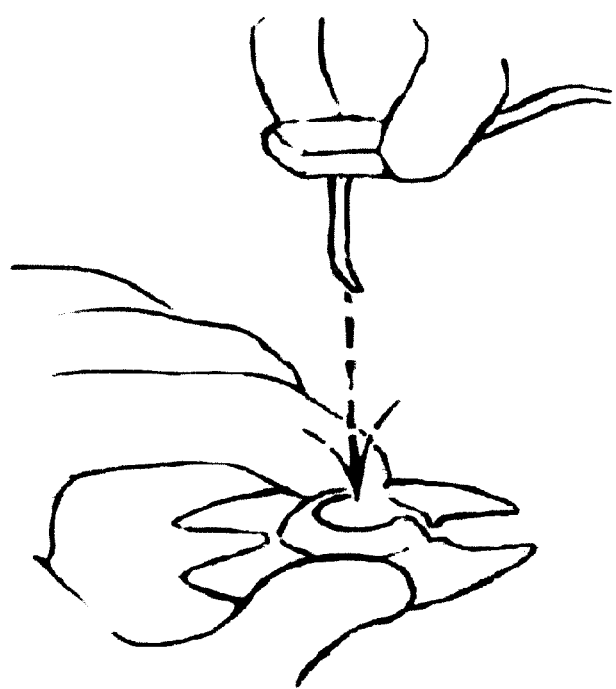
FIG. 11 is a schematic view illustrating the use of a device in accordance with the invention.

After the device has been positioned on the subcutaneous port the needle may be inserted as shown for example in FIG. 11. Once the needle is in place in the port, the device may be removed from the skin of the patient by simply deforming the device by separating the two opposing sides of the flange (3) along the channel (5), so that they pivot around the bridging section (8). The action is facilitated by the cut-away section (6) which closes as a result. Conveniently, the separation is achieved by holding one side of the channel (5) still and rotating the other side away in the plane of the skin. This has the effect of expanding the hole (2) substantially, (FIGS. 8-9) forming sufficient clearance for the device to be simply slid away from the port and needle.

EXAMPLE 3

Figure 8:
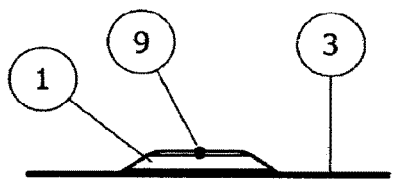
FIG. 8 is a side view of a modified form of the device of the invention.
Figure 9:
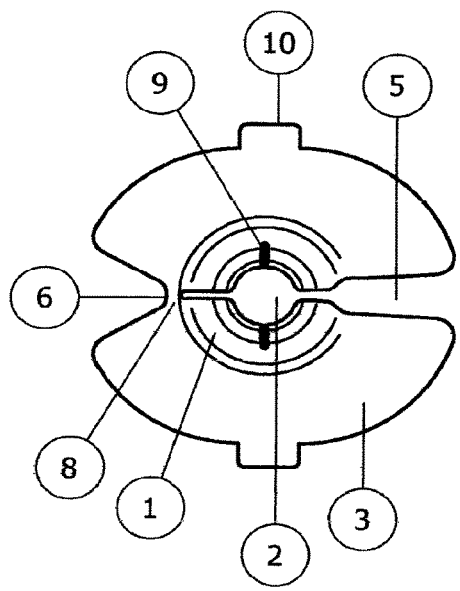
FIG. 9 is a top view of the device of FIG. 8.
Figure 10:
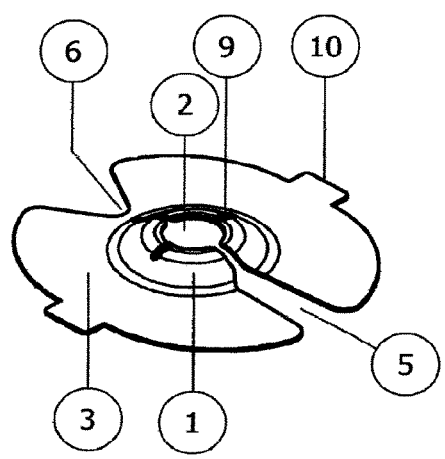
FIG. 10 is a perspective view of the device of FIG. 9.

A further device embodying the invention is shown in FIGS. 8-10. It comprises a circular disc of a transparent polypropylene, which is 0.5 mm thick. As before, a raised section or dome (1) is located in the centre of the disc and is shaped with essentially the same profile as a portacath. In this embodiment, the dome includes ridges at the base and a flattened upper surface in order to more closely fit over the port.

As before, a hole (2) is provided centrally in the top of the dome (1) and a substantially circular flange (3) extends outwardly from the base of the dome (1).

A radial section of the flange (3) is cut away to form a radial channel (5) extending outwardly from the dome (1) to accommodate the catheter line when in use. In addition, as in the embodiment of Example 2, a relatively wide v-shaped cutaway (6) is provided in one side of the flange (3). A narrow cut-out (7) extends from the channel (5) across the dome (1) and through the hole (2) towards the cut-away section (6) leaving only a small bridging section (8) holding the device together. This arrangement allows the bridging section (8) to act as a hinge to facilitate easy removal of the device, without disturbing the needle.

In addition, in this embodiment, markers (9) are provided on the upper surface of the dome to act as indicator or guide of the central plane for insertion of the needle. Furthermore, a pair of opposing laterally extending tabs (10) is provided on the edge of the flange (3) approximately perpendicular to an axis formed by the centre of the channels 5 and 7 and the cut-away section 6.

In use, the device, which is sterile, is applied to the skin of a patient in the region of a subcutaneous port (FIG. 11). The dome (1) of the device is pressed into a position in which it surrounds and engages the casing of the port so that it prevents relative movement between the port and the location device in the x/y plane. The wide flat base of the device formed by the flange (3) is pressed against the skin, which action pulls the port down tight against the body and prevents relative movement between the port and the device in the z plane. The device is orientated so that any bulges in the skin caused by the catheter line extending from the port are accommodated by the channel (5). In this way, the dome (1) constrains the movement of the underlying portacath, bringing it into alignment with the skin.

An injection using for instance a Huber needle can then be administered through the hole (2) which will be directly aligned with the central region of the septum of the portacath. Again, the use of the device improves the visibility of the portacath location.

Once the needle is in place in the port, the device of the invention may be hinged open, away from the needle, by pulling on the tabs (10) allowing the device to be removed without disturbing the needle.

The invention claimed is:

1. A device for positioning a subcutaneous port during an access procedure, said device comprising a dome of plastic material, said dome being shaped to fit directly over the subcutaneous port, and a flange extending laterally from the dome which is able to contact a surrounding skin area, wherein the device is a unitary device which comprises a cut-away section within the flange, aligned with an opposing channel in the flange such that the cut-away section and the opposing channel are separated by a hinge region, wherein rotation of opposing sides around the hinge region closes up the cut-away section and widens the opposing channel, to facilitate removal of the device from the surrounding skin area.

2. The device of claim 1 wherein the opposing channel is arranged to accommodate a catheter line extending from the port beneath skin.

3. The device of claim 1 wherein the cut-away section is v-shaped.

4. The device of claim 1 further comprising pull-tabs on edges of the flange to facilitate deformation of the device into the cut-away section.

5. The device of claim 1 which is of a substantially rigid plastic.

6. The device of claim 1 wherein a central region of the dome is provided with indicator means.

7. The device of claim 6 wherein the indicator means is a hole through which a needle may be inserted.

8. The device of claim 1 wherein the flange surrounds the dome.

9. The device of claim 8 wherein the opposing channel is provided in the flange to accommodate a catheter line extending from the port beneath skin.

10. The device of claim 1 which is in a sterile condition and is packaged in a sterile container.

11. A method for accessing a subcutaneous port, said method comprising positioning the device of claim 1 directly above said port so that the dome fits over the port and the flange makes direct contact with the surrounding skin area, then inserting a needle into the port through a central region in the dome, and thereafter deforming the device by causing rotation of the opposing sides around the hinge region such that the cut-away section closes up and the opposing channel widens, to allow removal from the surrounding skin area.

12. A kit comprising the device of claim 1, and one or more of disinfecting means and a needle.

13. The kit of claim 12 wherein the needle is a Huber needle.

14. The kit of claim 12 wherein each element of the kit is sterile and packaged in a sealed package or compartment.

\* \* \* \* \*